United States Patent [19]  [11] 4,020,842
Richman et al.  [45] May 3, 1977

[54] LINERLESS, RECLOSABLE TAB STOCK

[75] Inventors: Edward B. Richman, Shaker Heights; Seymour W. Tomlinson, Perry; Suzette Nemeth, Painesville; David W. Wilson, Mentor, all of Ohio

[73] Assignee: Avery International Corporation, San Marino, Calif.

[22] Filed: Oct. 23, 1975

[21] Appl. No.: 624,870

[52] U.S. Cl. .................... 128/287; 24/73 VA; 24/DIG. 11; 128/284; 428/40; 428/41; 428/352; 428/121; 428/124

[51] Int. Cl.² .................... A41B 13/02; B32B 3/04

[58] Field of Search .... 24/67 HR, 73 VA, DIG. 11; 428/40–43, 50, 354; 128/284, 287; 2/49 R, 50; 206/390, 411, 447, 484, 813

[56] References Cited
UNITED STATES PATENTS

| | | | |
|---|---|---|---|
| 2,248,317 | 7/1941 | Van Cleef | 206/813 |
| 3,257,228 | 6/1966 | Reed | 40/125 A |
| 3,383,121 | 5/1968 | Singer | 428/41 |
| 3,616,114 | 10/1971 | Hamaguchi et al. | 428/41 |
| 3,794,038 | 2/1974 | Buell | 128/287 |
| 3,833,456 | 9/1974 | Reed et al. | 128/287 |
| 3,848,594 | 11/1974 | Buell | 128/284 |
| 3,931,666 | 1/1976 | Karami | 128/287 |
| 3,943,609 | 3/1976 | Egan | 128/287 |
| 3,951,149 | 4/1976 | Ness et al. | 128/287 |

Primary Examiner—George F. Lesmes
Assistant Examiner—R. J. Roche
Attorney, Agent, or Firm—McNenny, Pearne, Gordon, Gail, Dickinson & Schiller

[57] ABSTRACT

A web construction of reclosable tab stock, particularly suited to low cost production and to high speed dispensing on automatic equipment by diaper manufacturers, but usable in other applications, has three substrates, one over the other, and each of which extends, transversely to machine direction and along its entire transverse length, substantially flatly and without folds.

10 Claims, 9 Drawing Figures

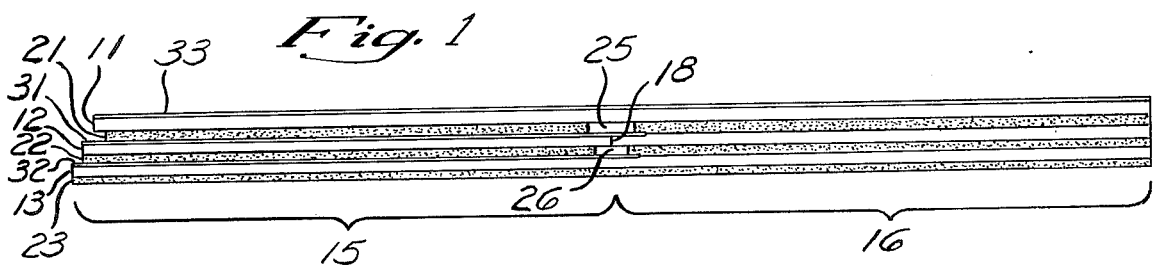
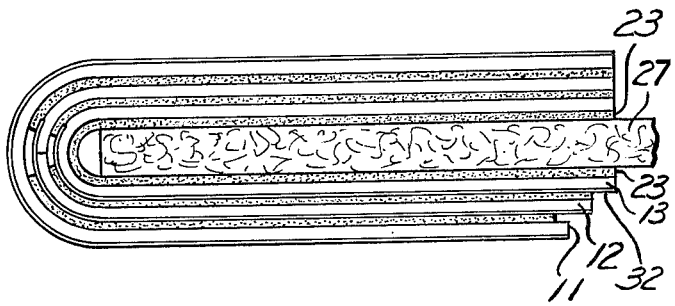
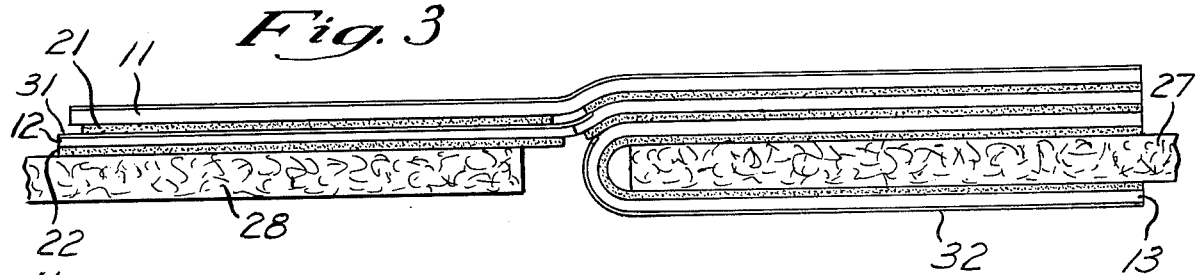
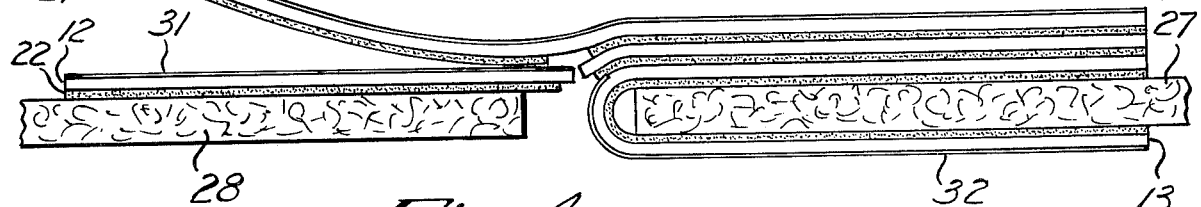
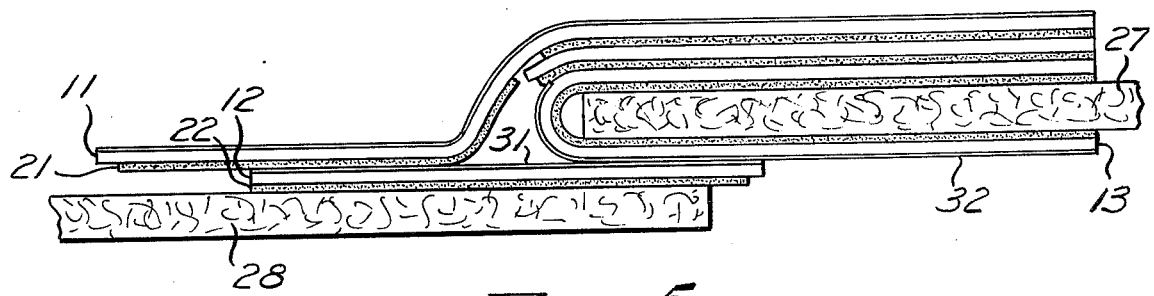

LINERLESS, RECLOSABLE TAB STOCK

This invention relates to laminate web constructions of linerless, reclosable tab stock of the kind adapted to be supplied to a diaper manufacturer and to be separated by the manufacturers into individual diaper tab constructions and applied to individual diapers, usually two tabs to a diaper. By "linerless" is meant the absence of any adhesive-protecting liner of release paper or the like that has to be separately disposed of by the person applying the diaper, either when the diaper is originally applied or when the diaper is reclosed after checking for continuing dryness and non-soiling.

To our knowledge, up to the present time there has been no provision of a diaper tab stock that can be manufactured by being formed of initially flat but flexible layers formed in long passes along the machine direction of a coating and laminating line and that is fabricatable completely by web coating, slitting and web-to-web laminating operations and without the necessity for folding operations, and which, when cut into short lengths and applied around the edges of diapers by high speed dispensing equipment of a diaper manufacturer, provides conveniently usable linerless reclosable diaper tabs. The present invention provides such a diaper tab stock.

Prior art diaper tab stock includes that shown in U.S. Pat. No. 3,833,456 to Reed and Komendat which is devoid of folds and suitable for dispensing on high speed equipment, but which is not reclosable. The prior also includes a resealable adhesive tape shown in U.S. Pat. No. 3,616,114 to Hamaguchi et al. that however includes folds and bulges and, if fabricated as diaper tab stock, would require folding operations and could be rolled for dispensing in high speed dispensing equipment only with great difficulty, if at all.

In the present invention three substrates are provided, one over the other, and each of which extends, transversely to machine direction and along its entire transverse length, substantially flatly and without folds. The second or intermediate substrate is divided by a slit at an intermediate point in its transverse length.

This construction can be fabricated completely by web coating, slitting, and web-to-web laminating operations, and without the necessity for folding operations, and can be readily rolled for storage, and shipment and for use in high speed dispensing on automatic equipment.

The laminate or construction comprising all three substrates is applied around the diaper edge by the diaper manufacturer. A parent can then peel the first two substrates from the third substrate along a portion of the length of the construction to expose a fastener tab consisting of the peeled portion of the first two substrates. This peeling is limited by the exhaustion of the extent of the associated release means. The diaper is then fastened to another part of the diaper. To reopen the diaper, the parent then peels the first substrate on such other part of the diaper from the second substrate. The peel-back force ends and the two diaper parts separate when the split in the second substrate is reached. During reopening a portion of the second substrate is left behind on such other part of the diaper. The diaper can then be reclosed if desired by rejoining the face portions of the first and second substrates that were newly exposed during reopening. This cycle can be repeated several times if desired.

In the drawings, the thicknesses of the webs and coatings are greatly exaggerated.

FIG. 1 is a schematic transverse elevation of diaper tab stock constructed according to the invention and then cut transversely to machine direction (machine direction being into the paper) into an individual laminate.

FIG. 2 is a view of the laminate shown in FIG. 1 as folded and fastened around the edge of one portion of a diaper by the diaper manufacturer.

FIG. 3 is a view of the same laminate, now peeled to form a tab which is joined to another portion of the diaper.

FIG. 4 is a view of the same laminate as shown in FIG. 3, now further peeled to temporarily or permanently separate the two portions of the diaper which had just been joined.

FIG. 5 is a view of the same laminate as shown in FIGS. 3 and 4, now reapplied to rejoin the two portions of the diaper.

Figure 3A:
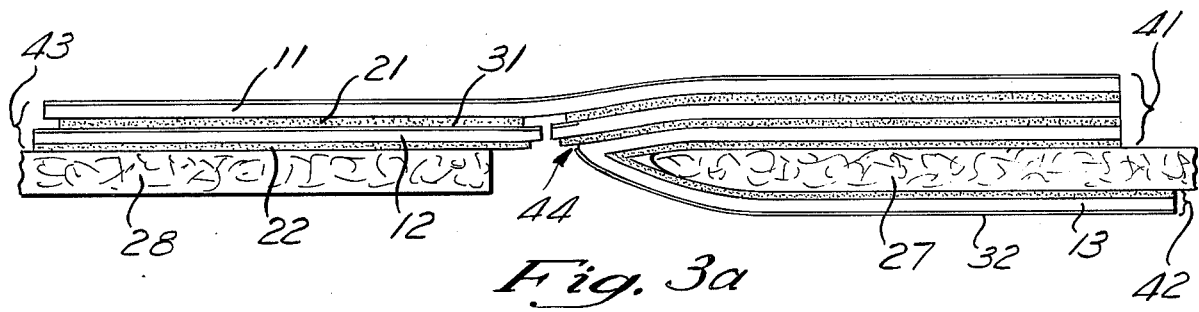
FIG. 3a is a view similar to FIG. 3 but schematically illustrating the laminate under tension.

The individual laminate seen in FIG. 1 is, in effect, a cross-sectional view of the diaper tab stock from which the individual laminate has been formed by transverse cuts. This stock, then, consists of initially flat but flexible layers suitable to be formed in long passes along the machine direction (into the paper as viewed in FIG. 1) of a coating and laminating line without the necessity for folding operations and completely by web coating, slitting and web-to-web laminating operations. These initially flat layers include a first substrate 11 which bears the first substrate adhesive 21 on its underside. The first substrate 11 and the first substrate adhesive 21 extend, transversely to machine direction, along first and second length portions 15 and 16 respectively of the web construction, the first substrate adhesive being divided from itself by a gap or skip 25.

A second substrate 12 bears second substrate adhesive 22 on its underside and also extends along the first and second length portions 15 and 16. First substrate release means is provided between the first substrate adhesive 21 and the second substrate 12, and may be a release coat 31 on the second substrate 12 as illustrated.

A third substrate 13 bears a third substrate adhesive 23 on its underside. Second substrate release means is provided between the second substrate adhesive 22 and the third substrate 13 and may comprise a release coat 32 on the third substrate 13 as illustrated.

The second substrate release means 32 is patterned to extend substantially only along the first length portion 15 and little if any into the second length portion 16. The first substrate release means may be similarly patterned, as shown for release means 31 in FIGS. 1 through 5, or it may be patterned to extend throughout both the first and second length portions as shown for release means 31a illustrated in FIG. 6. In the latter case the second substrate and its release coating may comprise commercially available release paper, a staple article of commerce which may be manufactured or purchased by the diaper tab stock manufacturer at relatively low cost.

The second substrate 12 is slit or divided along the machine direction in the region of adjacency of the first and second length portions, as at the slit 18.

A third substrate release means is provided between the third substrate adhesive 23 and another layer when the web construction is wound into roll form. In a preferred self-wound arrangement, the third substrate release means is on the first substrate 11 and may comprise a release coat 33 on this substrate.

It can be seen from FIG. 1 that the initially flat diaper tab construction at all points along the first and second length portions 15 and 16 has an overall thickness that does not exceed the total of the individual thicknesses of substrates 11 to 13, adhesives 21 to 23, and release coats 31 to 33. Each of the substrates, substrate adhesives, and release means, prior to dispensing of the web construction for application to diapers, extends along its entire transverse length substantially flatly and without folds, whether that length includes both length portions 15 and 16 or (as in the case of a certain release coating or coatings as described above) only one of such portions. Thus, the substrates 11, 12, and 13 extend along the lengths 15 and 16 flatly and without folds, the substrate 12 extending on both sides of the slit 18. The substrate adhesives 21, 22 and 23 extend along both length portions 15 and 16 flatly and without folds, the substrate adhesives 21 and 22 extending on both sides of their respective gaps 25 and 26. The release coats also extend flatly and without folds if provided as separate coatings, release coat 32 extending flatly and without folds through first portion 15 and release coating 31 extending through portion 15 alone or release coating 31a extending through both portions 15 and 16 depending upon whether the construction of FIGS. 1 to 5 or the construction of FIG. 6 is provided. Release coat 33 may extend flatly and without folds through both first and second portions 15 and 16.

Such a construction can be manufactured without folding operations and rolled on itself for storage, transport and high speed dispensing on automatic equipment.

Diaper tab stock having the cross section shown in FIG. 1 is wound on itself by the diaper tab stock manufacturer and is supplied in that form to the diaper manufacturer. High speed dispensing on automatic equipment requires only that the diaper tab stock be unwound, cut into individual laminates, and folded as individual laminates around the side edges of diapers in the manner illustrated in FIG. 2. As shown in FIG. 2 the individual laminate shown in FIG. 1 has been folded around a diaper portion 27 to be permanently joined thereto by the third substrate adhesive 23. The laminate is simply folded around the diaper edge as shown and pressed into place.

In use, the parent peels back the first length portions of the substrates 11 and 12 together from the substrate portion 13. The relative release at release coating 32 is easier than that at 31, so that the parent finds it easy to peel back both substrates 11 and 12 together. The peeled-back portions of the substrates 11 and 12 thereby form a tab as seen in FIG. 3, and this tab is joined to another portion 28 of the diaper by pressing the second substrate adhesive 22 against the diaper as also seen in FIG. 3.

When the diaper is to be removed or temporarily reopened, the substrate 11 is peeled back from the substrate 12 as shown in FIG. 4. The illustrated slight set-back of the first substrate adhesive 21 from the edge of the first substrate 11 is designed to assist the parent in starting this peel-back, the peel-back force requirement in this instance being higher than it was peeling back the substrate 12 from the substrate 13. As the peel-back is completed through the first length portion 15, the substrate 12 parts from itself at the split 18 as shown in FIG. 4. As this happens, the diaper portions 27 and 28 come apart and all peel-back force between substrates 11 and 12 disappears because the diaper portion 27 simply folds back as the substrate 11 continues to be pulled in the peel-back direction. Thus limitation of peel-back occurs when the split 18 is reached even if the release means in the form of a release coat 31a extends throughout the second length portion 16 as shown in FIG. 6, or the release means may terminate just beyond the split 18 as exemplified by the release coat 31 in FIGS. 1 to 5.

The diaper is reclosed, if desired, simply by repositioning the first length portion of the first substrate 11 over the first length portion of the second substrate 12 and pressing the first substrate adhesive 21 against the first substrate release means 31 on the second substrate 12. In accordance with familiar characteristics of pressure sensitive adhesives and release means therefor, the tensile strength of the joint between the first substrate adhesive 21 and the release means 31 is substantially stronger against lengthwise pulling force, such as the force which holds the diaper together, than it is against peel-back force, such as the force applied at the interface upon peeling back of the substrate 11. Thus the diaper remains firmly fastened upon reclosing, but can be readily reopened again. This cycle can be repeated a number of times if desired.

When the diaper is reclosed, the first length portion of the first substrate 11 need not necessarily be positioned over the first length portion of the second substrate 12, as just described. Instead, in some instances, the first substrate 11 may be drawn further over the diaper portion 28 so as to partly or totally bypass the first substrate portion 12, so that the first substrate adhesive 21 is positioned partly or even wholly directly over the diaper 28 rather than totally over the release means 31 on the second substrate 12. However those portions of the first substrate adhesive 21 that are directly positioned in this manner and then pressed against the diaper may be somewhat less readily unfastened (although a laminate can always readily be torn in half by the parent) or may become degraded by such direct contact and subsequent separation so that subsequent reclosure becomes less reliable to the extent that the degraded adhesive must be relied on. However pressing the tab into such direct contact can be avoided, if desired, if upon reclosing there is any reasonable extent of contact between the first substrate adhesive 21 and the first length portion of the second substrate 12, since such contact will establish adequate strength against the lengthwise pulling forces which must be resisted to keep the diaper closed. Such a partially overlapped relationship is shown in FIGS. 5 and 5a.

Such repositioning upon reclosure may be useful in reclosing the diaper in order to tighten the diaper on an infant, particularly if the diaper has stretched somewhat since its initial application, as may happen with those types of disposable diapers that tend to stretch during wearing.

Figure 3B:
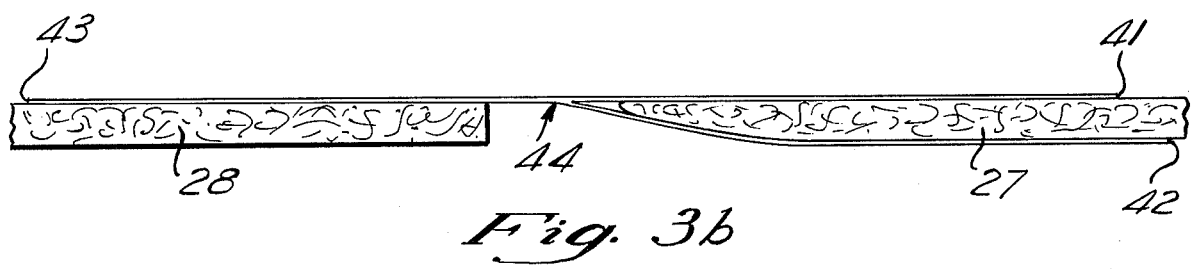
FIG. 3b is a view similar to FIG. 3a but more closely suggests the relative scale relationship of the thicknesses of the diaper and the laminate.
Figure 5A:
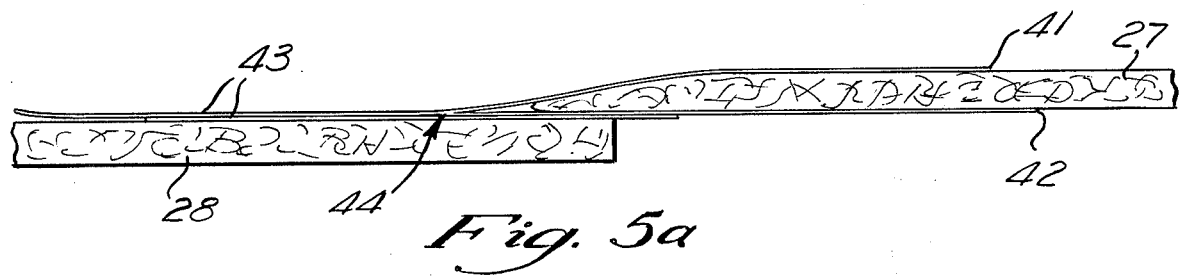
FIG. 5a is a view that bears the same relationship to FIG. 5 as FIG. 3b bears to FIG. 3 in that FIG. 5a illustrates the laminate under tension and also more closely suggests the relative scale relationship of the thicknesses of the diaper and the laminate.
Figure 6:
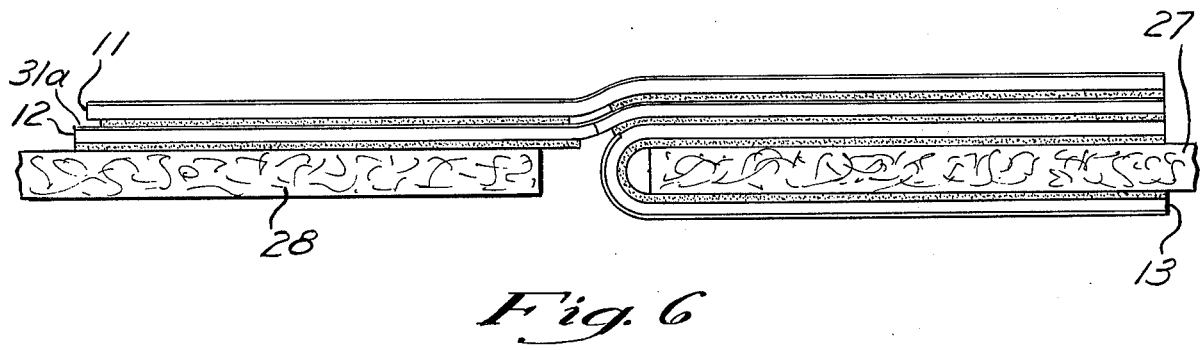
FIG. 6 is a view similar to FIG. 3 but showing a slightly different laminate embodying the invention.

FIGS. 3a, 3b and 5a suggest the configuration that the laminate actually has in use when tension is applied between the diaper portions 27 and 28. As can be seen, the laminate tends to have a Y-configuration, with the elements to the left, as viewed, forming the base 43 of the Y and the elements to the right by dividing into the two legs or branches of the Y, labelled 41 and 42. The point of forking (i.e. the limit of the "area divarication" which occurs between the second and third substrates), indicated by the reference numeral 44, tends to form at the point between the second substrate adhesive 22 and the third substrate 13 where the release coat 32 terminates.

The Y-configuration divides the tension load at the diaper portion 27 between the two legs 41 and 42. The provision of a tension-dividing Y-configuration is inherent in constructions of the "area-divarication" type, such as that shown in Reed and Komendat U.S. Pat. No. 3,833,456, previously mentioned. In the present invention such inherency is advantageously exploited in a novel reclosable construction.

As will be evident to those skilled in the art, the gaps 25 and 26 in the first and second substrate adhesive 21 and 22 are provided to keep the first and second length portions of each substrate adhesive definitely separated so that there will be no "bridging" of either adhesive across the slit 18. This helps assure that the separation at the slit 18 will be clean and positive, and makes it easier for the parent to effect the desired separation in the intended manner. The slit 18 itself need not be a complete slit, but may be a partial cut, line of perforations, or other line of weakening, which will allow ready separation between the first and second length portions of the second substrate 12.

The first substrate should have high tensile and tear strength, and may be a paper reinforced by fiber scrim or resin or rubber fillers, an example being Endura paper manufactured by W.R. Grace Company. Typical thickness is 4–10 mils, but the substrate may be thinner.

The second substrate should have high internal strength and may comprise the same materials mentioned in respect of the first substrate. Typical thickness is 3–7 mils, but the substrate may be thicker.

The third substrate is preferably a supercalendered or "densified" kraft paper such as "semi-bleached release sheet" manufactured by The Weyerhaeuser Company. Typical thickness is 2–4 mils, but the substrate may be thicker.

Any of the above substrates may be made from reinforced papers, plastic fibers, or synthetic papers made from plastic films.

Typical adhesive film thicknesses are 1–3 mils, and any suitable conventional pressure sensitive adhesives and/or (in the case of the third substrate) heat activated adhesive may be used.

The release means, particularly those that extend across both the first and second length portions, may be other than the illustrated release coatings. The face or surface of some plastic substrate materials may inherently provide acceptable peel-back release for adjacent substrate adhesives. The third substrate release means such as 33 may be replaced by a separate release liner (not shown) which protects the third substrate adhesive 23 until disposed of by the diaper manufacturer. Such a product is nevertheless linerless in the sense previously mentioned because no liner remains after application of the product to a diaper by the manufacturer. Thus any of the release means may be the face or surface of one of the substrates, if such substrate is a plastic having suitable release characteristics, and the third substrate release means may be a release coating on a separate release paper, or simply the face of an inherently releasable separate plastic film. The construction can be provided in sheeted rather than rolled form, but the efficiencies of roll feeding during manufacturing are thereby lost. In the illustrated embodiment sheeting presents some problem because a small portion of each sheet's adhesive 23 is exposed due to the fact that the substrate 11 is shorter than the substrate 13.

The first substrate release means, if not the surface of a plastic film, can be any suitable release coating known in the art, such as silicones, polyvinyls, acrylics, or metal complexes of fatty acids such as DuPont's Quillon. Typical release levels are 400–2000 grams per inch width (separating force peeling at 180° at 12 inches per minute). The first substrate release means must have the highest of the release levels.

The second substrate release means can be any of the foregoing release means. Typical release levels are 10–200 grams per inch width, but may be greater.

The third substrate release means if provided in the self-wound construction can be any of the foregoing release means. Typical release levels are again 10–200 grams per inch width but may be greater. The release level should preferably be slightly less than that of the second release means.

The invention can be used in other applications where there is a need for providing a reclosable tab at low cost that provides for inherent registration of the reclosable interface of the tab (e.g. the reclosable interface between elements 21 and 31 in the illustrated embodiment) rather than requiring that the two elements defining the reclosable interface be separately applied in proper registration by the manufacturer of the product (e.g. envelopes, cartons, surgical gowns, disposable garments, sheets, covers or the like).

The invention is not restricted to the slavish imitation of each and every detail set forth above. Obviously, devices may be provided which change, eliminate, or add certain specific details without departing from the invention.

What is claimed is:

1. A diaper having a reclosable diaper tab formed of diaper tab stock comprising a web construction of linerless reclosable diaper tab stock made up of initially flat but flexible layers suitable to be formed in long passes along the machine direction of a coating and laminating line and to be rolled up for storage and shipment, and unrolled for use by diaper manufacturers, and fabricatable completely by web coating, slitting and web-to-web laminating operations and without the necessity for folding operations, and suitable for high speed dispensing on automatic equipment, including a first substrate bearing first substrate adhesive on its underside, and extending, transversely to machine direction, along first and second length portions, a second substrate bearing second substrate adhesive on its underside and extending along said first and second length portions, first substrate release coat means below said first substrate adhesive and associated with said second substrate, a third substrate bearing a third substrate adhesive on its underside, second substrate release coat means below said second substrate adhesive and associated with said third substrate at said first length portion and patterened to extend substantially only along said first length portion and substantially none into said second length portion, said second substrate being slit or divided along the machine direction in the region of adjacency of said first and second length portions.

2. A diaper having a reclosable diaper tab formed of diaper tab stock comprising a web construction of linerless reclosable tab stock comprising first, second and third flat and unfolded substrates positioned one over the other and each carrying its own substrate adhesive on its underside, and each extending, transversely to machine direction, along first and second length portions, said second substrate being slit or divided in the region of adjacency of said first and second length portions, first substrate release coat means associated with said second substrate below said first substrate adhesive and extending at least along said first length portion, and second substrate release coat means associated with said third substrate below said second substrate adhesive and extending only along said first length portion and substantially none into said second length portion.

3. Linerless reclosable tab stock as in claim 2, said second substrate release coat means comprising a release coating on said third substrate.

4. In a diaper having a reclosable diaper tab formed of diaper tab stock comprising a web construction of linerless reclosable tab stock adapted to be wound into roll form, a first substrate bearing first substrate adhesive on its underside, and extending, transversely to machine direction, along first and second length portions, a second substrate bearing second substrate adhesive on its underside and extending along said first and second length portions, first substrate release coat means below said first substrate adhesive and associated with said second substrate, a third substrate bearing a third substrate adhesive on its underside, second substrate release coat means below said second substrate adhesive and associated with said third substrate at said first length portion and patterned to extend substantially only along said first length portion and substantially none into said second length portion, third substrate release coat means below said third substrate adhesive and associated with another layer when said web construction is wound into roll form, said second substrate being slit or divided along the machine direction in the region of adjacency of said first and second length portions.

5. In web construction of linerless reclosable diaper tab stock made up of initially flat but flexible layers suitable to be formed in long passes along the machine direction of a coating and laminating line and to be rolled up for storage and shipment, and unrolled for use by diaper manufacturers, and fabricatable completely by web coating, slitting and web-to-web laminating operations and without the necessity for folding operations, and suitable for high speed dispensing on automatic equipment, a first substrate bearing first substrate adhesive on its underside, and extending, transversely to machine direction, along first and second length portions, a second substrate bearing second substrate adhesive on its underside and extending along said first and second length portions, first substrate release coat means below said first substrate adhesive and associated with said second substrate, a third substrate bearing a third substrate adhesive on its underside, second substrate release coat means below said second substrate adhesive and associated with said third substrate at said first length portion and patterned to extend substantially only along said first length portion and substantially none into said second length portion, said second substrate being slit or divided along the machine direction in the region of adjacency of said first and second length portions, said construction at all points along said first and second length portions having an overall thickness that does not exceed the total of: the sum of the single thicknesses of said first, second and third substrates plus the sum of the additional single thicknesses of adhesive respectively associated with said substrates plus the sum of the additional single thicknesses of release coat means associated with said substrates.

6. A diaper having a reclosable diaper tab formed of diaper tab stock comprising a linerless reclosable tab stock web construction adapted to be wound into roll form including a first substrate bearing first substrate adhesive on its underside, and extending, transversely to machine direction, along first and second length portions, a second substrate bearing second substrate adhesive on its underside and extending along said first and second length portions, first substrate release coat means below said first substrate adhesive and associated with said second substrate, a third substrate bearing a third substrate adhesive on its underside, second substrate release coat means below said second substrate adhesive and associated with said third substrate at said first length portion and patterned to extend substantially only along said first length portion and substantially none into said second length portion, third substrate release coat means associated with said first substrate and positioned below said third substrate adhesive when said web construction is wound into roll form, said second substrate being slit or divided along the machine direction in the region of adjacency of said first and second length portions.

7. In a diaper having a reclosable diaper tab formed of diaper tab stock comprising a web construction of linerless reclosable tab stock, a first substrate bearing first substrate adhesive on its underside, and extending, transversely to machine direction, along first and second length portions, a second substrate bearing second substrate adhesive on its underside and extending along said first and second length portions, first substrate release coat means below said first substrate adhesive and associated with said second substrate at both said length portions, a third substrate bearing a third substrate adhesive on its underside, second substrate release coat means below said second substrate adhesive and associated with said third substrate at said first length portion and patterned to extend substantially only along said first length portion and substantially none into said second length portion, said second substrate being slit or divided along the machine direction in the region of adjacency of said first and second length portions.

8. A web construction of linerless reclosable tab stock for use in the manufacture of diapers, said web construction including a first substrate bearing first substrate adhesive on its underside, and extending, transversely to machine direction, along first and second length portions, a second substrate bearing second substrate adhesive on its underside and extending along said first and second length portions, first substrate release coat means below said first subtrate adhesive and associated with said second substrate, a third substrate bearing a third substrate adhesive on its underside, second substrate release coat means below said second substrate adhesive and associated with said third substrate at said first length portion and patterned to extend substantially only along said first length portion and substantially none into said second length portion, said second substrate being slit or divided along the machine direction in the region of adjacency of said first and second length portions, each of said substrates, prior to dispensing of said web construction for application to diapers, extending, transversely to machine direction and along its entire transverse length and on each side of any slits in itself, substantially flatly and without folds.

9. In web construction of linerless reclosable tab stock for use in the manufacture of diapers, a first substrate bearing first substrate adhesive on its underside, and extending, transversely to machine direction, along first and second length portions, a second substrate bearing second substrate adhesive on its underside and extending along said first and second length portions, first substrate release coat means below said first substrate adhesive and associated with said second substrate, a third substrate bearing a third substrate adhesive on its underside, second substrate release coat means below said second substrate adhesive and associated with said third substrate at said first length portion and patterned to extend substantially only along said first length portion and substantially none into said second length portion, said second substrate being slit or divided along the machine direction in the region of adjacency of said first and second length portions, each of said substrates, substrate adhesives and release coat means, prior to dispensing of said web construction for application to diapers, extending, transversely to machine direction and along its entire transverse length and at both sides of any gaps, skips or slits in itself, substantially flatly and without folds.

10. A linerless reclosable diaper tab stock web construction made up of initially flat but flexible layers suitable to be formed in long passes along the machine direction of a coating and laminating line and to be rolled up for storage and shipment, and unrolled for use by diaper manufacturers, and fabricatable completely by web coating, slitting and web-to-web laminating operations and without the necessity for folding operations, and suitable for high speed dispensing on automatic equipment, including, a first substrate bearing first substrate adhesive on its underside, and extending, transversely to machine direction, along first and second length portions, a second substrate bearing second substrate adhesive on its underside and extending along said first and second length portions, first substrate release coat means below said first substrate adhesive and associated with said second substrate, a third substrate bearing a third substrate adhesive on its underside, second substrate release coat means below said second substrate adhesive and associated with said third substrate at said first length portion and patterned to extend substantially only along said first length portion and substantially none into said second length portion, third substrate release coat means associated with said first substrate and positioned below said third substrate adhesive when said web construction is wound into roll form, said second substrate being slit or divided along the machine direction in the region of adjacency of said first and second length portions, said construction at all points along said first and second length portions having an overall thickness that does not exceed the total of: the sum of the single thickness of said first, second and third substrates plus the sum of the additional single thicknesses of adhesive respectively associated with said substrates plus the sum of the additional single thicknesses of release coat means associated with said substrates, each of said substrates, substrate adhesive and release coat means, prior to dispensing of said web construction for application to diapers, extending, transversely to machine direction and along its entire transverse length and at both sides of any gaps, skips or slits in itself, substantially flatly and without folds.

* * * * *